(12) United States Patent
Ridenour et al.

(10) Patent No.: US 7,845,225 B2
(45) Date of Patent: Dec. 7, 2010

(54) ANALYZING GRIP PRESSURE OF A BOWLER

(75) Inventors: Paul J. Ridenour, Waukesha, WI (US);
Neil B. Stremmel, Grand Prairie, TX (US); Bill Monce, Wheaton, IL (US);
James E. Jaryszak, Mansfield, TX (US)

(73) Assignee: United States Bowling Congress, Inc., Arlington, TX (US)

( * ) Notice: Subject to any disclaimer, the term of this patent is extended or adjusted under 35 U.S.C. 154(b) by 144 days.

(21) Appl. No.: 12/360,155

(22) Filed: Jan. 27, 2009

(65) Prior Publication Data
US 2009/0199636 A1      Aug. 13, 2009

Related U.S. Application Data

(60) Provisional application No. 61/027,697, filed on Feb. 11, 2008, provisional application No. 61/027,700, filed on Feb. 11, 2008.

(51) Int. Cl.
*A61B 5/22* (2006.01)

(52) U.S. Cl. .................................. 73/379.02

(58) Field of Classification Search .............. 73/379.02; 702/138; 473/61
See application file for complete search history.

(56) References Cited

U.S. PATENT DOCUMENTS

| | | | |
|---|---|---|---|
| 3,323,367 A | 6/1967 | Searle | |
| 3,897,058 A | 7/1975 | Koch | |
| 4,861,034 A | 8/1989 | Lee | |
| 5,033,291 A | 7/1991 | Podoloff et al. | |
| 5,118,112 A | 6/1992 | Bregman et al. | |
| 5,221,088 A | 6/1993 | McTeigue et al. | |
| 5,251,903 A | 10/1993 | Bixler et al. | |
| 5,316,479 A | 5/1994 | Wong et al. | |
| 5,322,289 A | 6/1994 | Abrams et al. | |
| 5,343,445 A | 8/1994 | Cherdak | |
| 5,372,365 A | 12/1994 | McTeigue et al. | |
| 5,419,563 A | 5/1995 | Abrams et al. | |
| 5,431,395 A | 7/1995 | Ganger, Sr. | |
| 5,542,676 A | 8/1996 | Howe, Jr. et al. | |
| 5,878,378 A | 3/1999 | Brommer et al. | |
| 5,885,229 A | 3/1999 | Yamato et al. | |
| 5,957,870 A | 9/1999 | Yamato et al. | |

(Continued)

OTHER PUBLICATIONS

Jowdy, John, "Bowling Execution", 2nd Edition, pp. 54, 60,61, 63,64, 67,68, and 71, 2002.

*Primary Examiner*—Jewel Thompson
(74) *Attorney, Agent, or Firm*—Michael Best & Friedrich LLP (57) ABSTRACT

Systems and methods for measuring and analyzing the grip of a bowler. In some embodiments, a bowling grip pressure device includes a glove configured to leave the second finger, the third finger, and the thumb substantially exposed. Pressure sensors are attached to the substantially exposed fingers. At least one pressure sensor is permanently affixed to the glove. Methods are taught for analyzing a bowler's performance. In some embodiments, the bowler performs a plurality of bowling motions. Pressures exerted on the second finger, the third finger, and the thumb are measured and recorded as a function of time. The bowler's performance is evaluated based upon the recorded pressures as a function of time. Methods are also taught for using recorded grip pressure data to fit a bowler with a proper bowling ball.

28 Claims, 7 Drawing Sheets

U.S. PATENT DOCUMENTS

| | | |
|---|---|---|
| 6,231,527 B1 | 5/2001 | Sol |
| 6,441,745 B1 | 8/2002 | Gates |
| 6,567,536 B2 | 5/2003 | McNitt et al. |
| 6,616,556 B1 | 9/2003 | Osmudsen |
| 6,716,034 B2 | 4/2004 | Casanova, Jr. et al. |
| 6,807,869 B2 | 10/2004 | Farringdon et al. |
| 6,836,744 B1 | 12/2004 | Asphahani et al. |
| 6,905,339 B2 | 6/2005 | DiMare et al. |
| 7,089,152 B2 | 8/2006 | Oda et al. |
| 7,264,553 B1 * | 9/2007 | Addington et al. ............ 473/61 |
| 7,431,657 B2 * | 10/2008 | Whitehead et al. ............ 473/59 |
| 7,477,504 B1 * | 1/2009 | Delida ........................ 361/230 |
| 2003/0054327 A1 | 3/2003 | Evensen |
| 2008/0189827 A1 * | 8/2008 | Bauer ........................ 2/161.2 |

* cited by examiner

ANALYZING GRIP PRESSURE OF A BOWLER

RELATED APPLICATIONS

This patent application claims priority to U.S. Provisional Patent Applications Ser. No. 61/027,697 filed Feb. 11, 2008, and 61/027,700, filed Feb. 11, 2008, the entire contents of which are both herein incorporated by reference.

FIELD OF INVENTION

The invention relates generally to methods and systems for athletic training and performance analysis of bowlers and, in particular, to methods and systems for measuring and analyzing grip pressure during a bowling motion.

BACKGROUND

Systems are known that assist individuals in improving grip in athletic activities, specifically in sports such as golf, tennis, and baseball that involve swinging a striking implement. These previous systems detect and alert the athlete when total grip pressure exceeds or falls below a certain threshold.

SUMMARY

While some attempts have been made to analyze grip in the above mentioned sports, detailed analysis of bowling motions has, in general, not been conducted. Bowling coaching has generally been limited by what can be perceived by human senses. However, the fluid motion of an ideal bowling movement can be greatly affected by changes in grip that are not perceptible to a human. As such, coaches and equipment fitters have been limited in their ability to coach and fit bowlers.

Some embodiments of the invention provide a bowling grip pressure device comprising a glove and a plurality of pressure sensors. The glove includes two sheaths to accept and cover a first finger and a fourth finger. The glove includes three openings to accept and leave substantially exposed a second finger, a third finger, and a thumb. The device includes pressure sensors permanently affixed to the glove that align with the first and fourth fingers between the finger tip and the distal interphalangeal joint. Additional sensors are included that are temporarily attached to the second finger and the third finger between the finger tip and the distal interphalangeal joint and to the thumb between the finger tip and the proximal interphalangeal joint when worn by a bowler. In some embodiments, the bowling grip pressure device also includes a communication interface and a computer.

Some embodiments of the invention provide methods of analyzing a bowler's performance. A bowler performs a plurality of bowling motions while the pressures exerted on each of a second finger, a third finger, and a thumb are measured and recorded as functions of time. A measurement set is created for each bowling motion. The bowler's performance is evaluated based upon the recorded pressures as a function of time.

Some embodiments of the invention provide methods of fitting a bowler with a bowling ball. The bowler performs a bowling motion with a first bowling ball while the pressures exerted on each of a second finger, a third finger, and a thumb are measured as functions of time. A measurement set is created for each bowling motion. The fit of the first bowling ball for the bowler is evaluated based on the recorded pressures as a function of time. In some embodiments, the bowler repeats the bowling motion a plurality of times with the first ball. In some embodiments, the bowler repeats the motion at least once with a second ball. In some embodiments, either the first ball or the second ball is selected as the better fit for the bowler by comparing the measurement sets collected with each ball.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
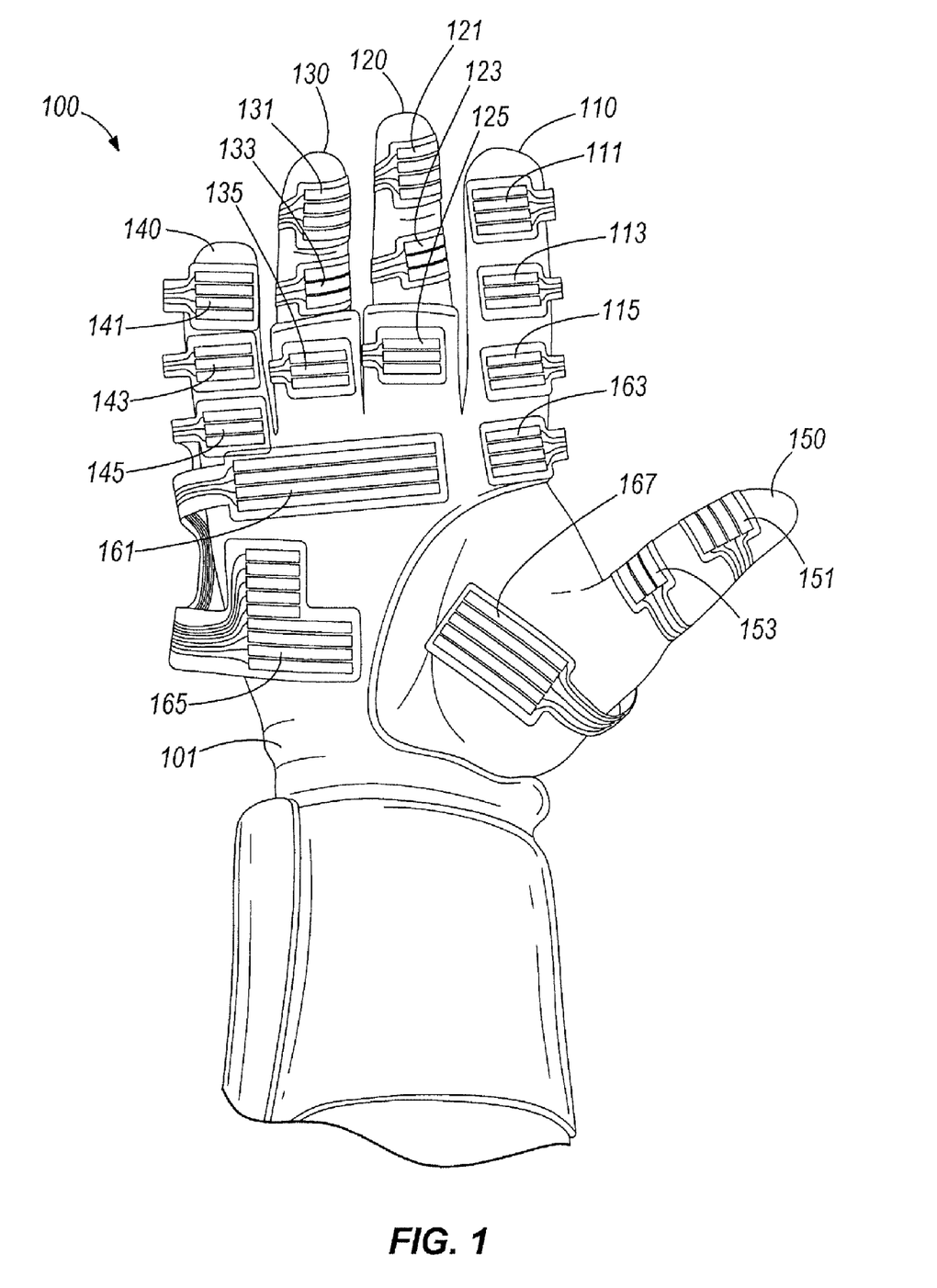
FIG. 1 is an illustration of a hand fitted with a pressure sensing apparatus according to one embodiment.

FIG. 1 illustrates one construction of a pressure sensing apparatus 100 as worn by a bowler. The pressure sensing apparatus 100 in this construction includes a glove 101 and a plurality of pressures sensors. A suitable commercially available system of sensors is the Grip® VersaTek® System from Tekscan, Inc. In the VersaTek® System, each pressure sensor has an array of twelve to sixty individual sensing units that provide a two-dimensional array of pressure distribution across the sensor. The pressure sensing apparatus may include less complex sensors as well as more or fewer pressure sensors than are shown in this construction. References to fingers and sensors below that use 100 series reference characters (e.g., 110 for the first finger, 120 for the second finger, etc.) refer to those shown in FIG. 1 unless explicitly stated otherwise.

In this construction, some pressure sensors are permanently affixed to the glove 101. Among other benefits, this reduces the amount of time involved in equipping the bowler with the pressure sensing apparatus 100. Sensor 111 and sensor 141 are affixed to glove 101 and positioned to align with the first finger 110 and the fourth finger 140, respectively, between the finger tip and the distal interphalangeal joint when worn. Similarly, sensor 113 and sensor 143 are positioned to align with the first and fourth fingers (110 and 140) between the distal interphalangeal joint and the proximal interphalangeal joint. Sensor 115 and 145 are positioned to align with the first and fourth fingers (110 and 140) between the proximal interphalangeal joint and the metacarpophalangeal joint. Sensor 161 is positioned to extend across the metacarpophalangeal joints of the second, third, and fourth fingers (120, 130, and 140) while sensor 167 is positioned over the metacarpophalangeal joint of the first finger 110. Sensor 165 is positioned at the outer palm of the bowler's hand.

Other pressure sensors are not permanently affixed to the glove 101. Because the fingers that will be inserted into the bowling ball (the second finger 120, the third finger 130, and the thumb 150) are not covered by glove 101, sensors are temporarily affixed to the bowler's skin when wearing the pressure sensing apparatus 100. As a consequence, sensor 121 and sensor 131 are attached directly to the skin of the bowler's second finger 120 and third finger 130, respectively, between the finger tip and the distal interphalangeal joint. Similarly, sensor 123 and sensor 133 are attached to the skin of the bowler's second and third fingers (120 and 130) between the distal interphalangeal joint and the proximal interphalangeal joint. Sensor 151 and sensor 153 are attached to the skin of the thumb 150 between the finger tip and the proximal interphalangeal joint and between the proximal interphalangeal joint and the metacarpophalangeal joint, respectively. Sensor 167 is attached to the palm of the bowler's hand. These sensors can be attached to the skin with medical tape or adhesive compatible with use on human skin.

Figure 2:
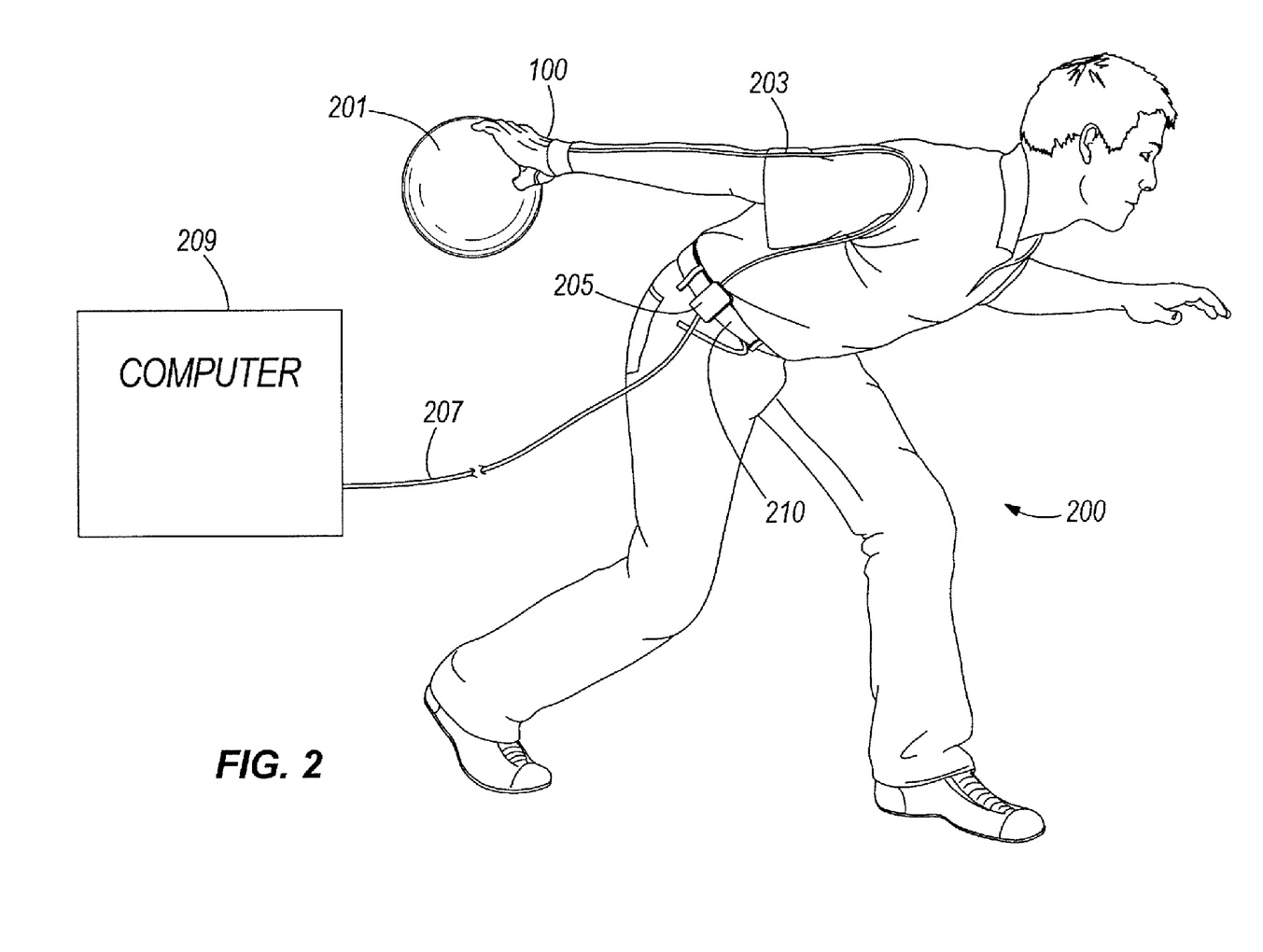
FIG. 2 is an illustration of interconnections of the pressure sensing apparatus of FIG. 1 and a computerized pressure monitoring system according to one construction.

FIG. 2 shows a bowler 200 equipped with the pressure sensing apparatus 100 and associated monitoring equipment according to one construction. The pressure sensing apparatus 100 is connected to a communication device 205 through cable 203. Communication device 205 is further connected to the computer 209 through cable 207. The bowler performs a bowling motion with bowling ball 201. Communication device 205 receives pressure measurement data from the pressure sensing apparatus 100 and forwards it to computer 209 where it is displayed, interpreted, and analyzed.

The system shown in FIG. 2 may be modified in a variety of ways. For example, in some constructions, communication device 205 is worn on the belt 210 (as pictured in FIG. 2), while in other constructions, it is permanently affixed to glove 101. In some constructions communication device 205 sends data to computer 209 through wireless means such as radio frequency (RF). In some constructions computer 209 is a standard desktop personal computer whereas in other constructions it is a computerized hardware device designed specifically for monitoring and analyzing grip pressure.

Figure 3:
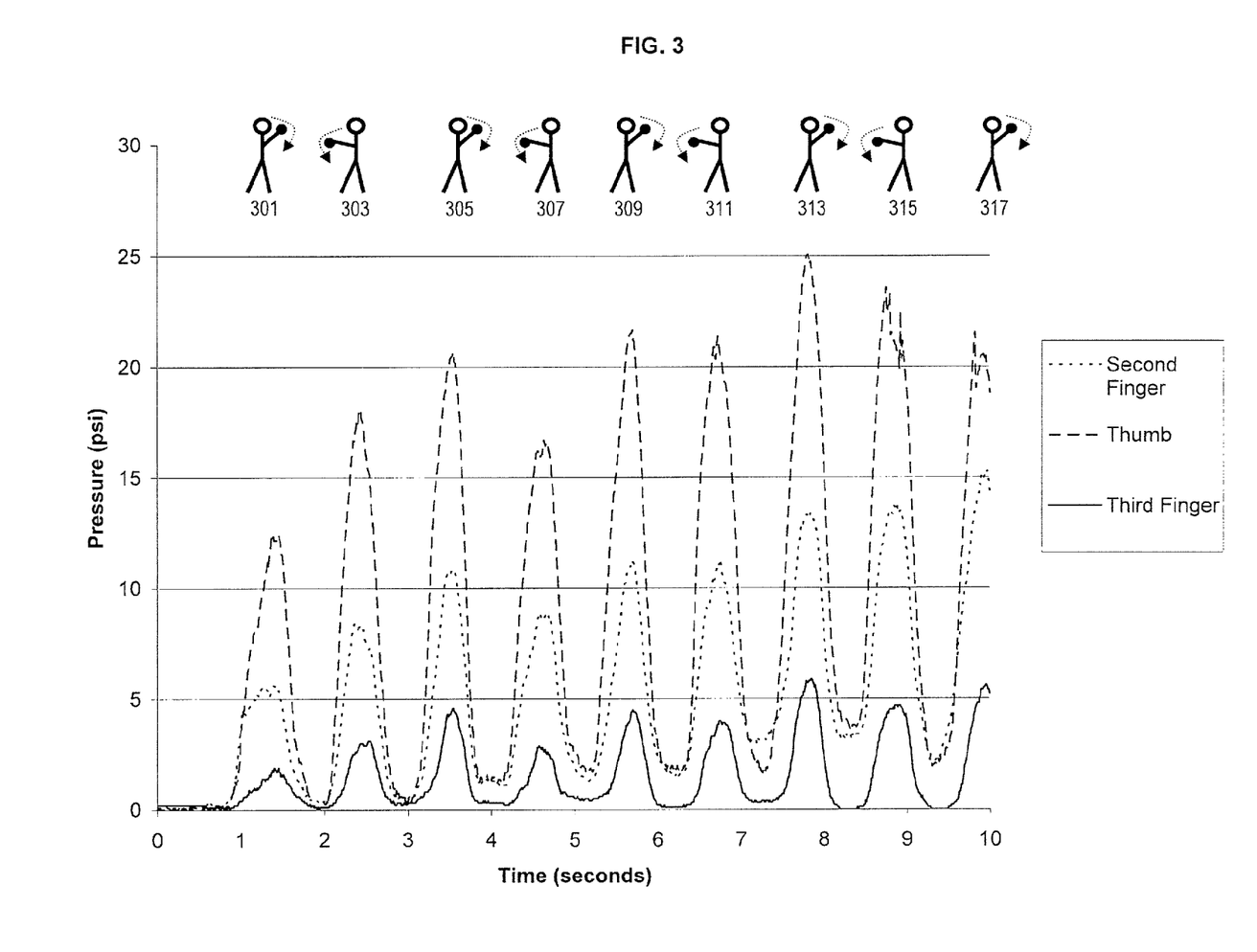
FIG. 3 is a graph showing the pressure exerted by three fingers and the corresponding position of the bowler as functions of time as a bowler swings a ball back and forth without releasing.

FIG. 3 demonstrates the grip pressure of a bowler during a bowling motion. A bowler is equipped with the system shown in FIG. 2, grips a bowling ball, and swings the bowling ball back and forth without releasing. References to fingers and sensors below that use 100 series reference characters (e.g., 110 for the first finger, 120 for the second finger, etc.) refer to those shown in FIG. 1, unless explicitly stated otherwise. The graph in FIG. 3 shows the pressure detected by sensor 151 (shown as "Thumb"), sensor 121 (shown as "Second Finger"), and sensor 131 (shown as "Third Finger").

Above the graph are a series of images 301, 303, 305, 307, 309, 311, 313, 315, and 317 that show the approximate position of the ball in the bowler's swing at the time corresponding to the graph. A period of relatively low grip pressure occurs as the ball approaches the top of the back swing and, in this case, the top of the forward swing. This is because the pressure on the individual fingers decreases as momentum and speed decrease.

When the ball is held motionless in front of the bowler (from 0 seconds to approximately 1 second), the grip pressure detected on all three plotted fingers is relatively low. However, as the bowler begins swinging backwards (301) the grip detected at all three plotted fingers increases. The grip pressure decreases when the ball approaches the top of the bowler's backswing and again increases when the bowler begins swinging the ball forward (303).

In a fluid bowling motion, these peaks and depressions are fairly smooth and curvilinear. However, this analysis also detects when a bowler deviates from a repeatable fluid motion. For example, the relatively high pressure measured at position 315 shows three different spikes of pressure on thumb 150 as detected by sensor 151. These spikes might be caused, for example, by the bowler attempting to change the speed or direction of the ball by grabbing it during the forward swing. This sporadic pressure affects the motion of the swing and, therefore, affects the performance of the ball when released. Such a reaction may not be perceptible to a coach or even to the bowler, but it can be detected and analyzed using embodiments of the invention.

Figure 4:
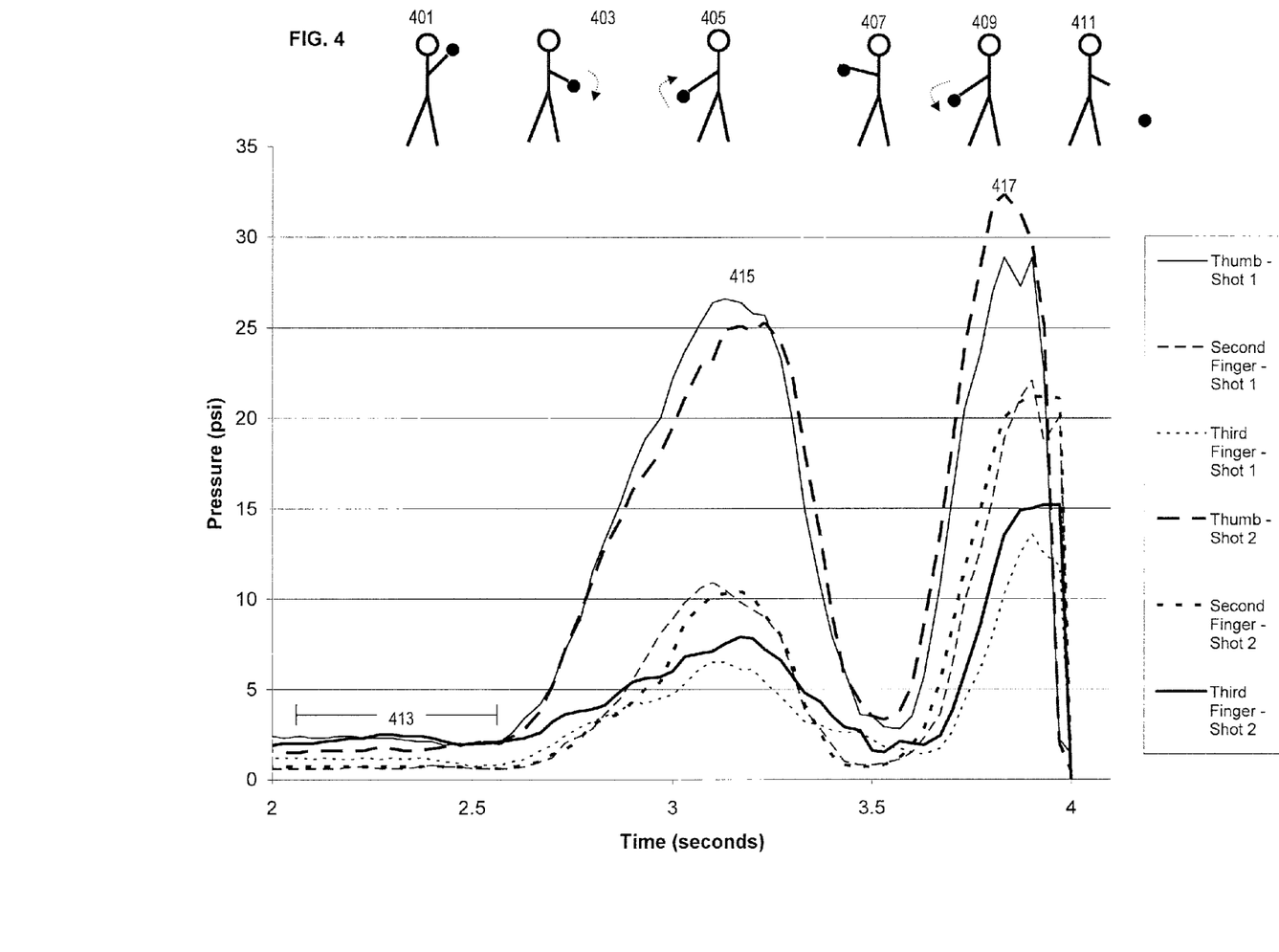
FIG. 4 is a graph comparing two sets of finger pressure data and the corresponding position of the bowler as functions of time during a bowler's approach and release.

The graph shown in FIG. 4 plots finger pressures measured during a bowler's actual approach and release of the ball. The bowler performed the same type of shot twice (Shot 1 and Shot 2) and the six sets of data shown on the graph of FIG. 4 correspond to the pressures measured on the thumb, the second finger, and the third finger during each of the two bowling shots. The legend to the right of the graph defines the sensor and the shot corresponding to each data set. Above the graph are a series of images 401, 403, 405, 407, 409, and 411 that show the approximate position of the ball in the bowler's swing at the time corresponding to the graph. At position 401, the bowler is holding the ball in a cupped hand. At position 403, the bowler has begun lowering the ball into his backswing. The ball rises into the backswing at position 405 and reaches the top of the backswing at position 407. At position 409, the bowler begins to bring the ball forward until releasing the ball at position 411.

During both Shot 1 and Shot 2, the pressure detected on the fingers was relatively low while the bowler is holding the ball before beginning her approach (position 401) as shown by the pressure curves between approximately 2 and 2.5 seconds (delineated as portion 413). A rise in pressure is detected at each finger when the bowler begins moving the ball backwards (position 403) as indicated by the portion of the curve depicting a first period of relatively high pressure measurements (peak 415). This pressure decreases as the bowler approaches the top of her backswing (position 405). Relatively low pressures are detected on the fingers at the top of the backswing (position 407). However, grip pressure rises again when the bowler begins to move the ball forward (position 409) as indicated by the portion of the curve depicting a second period of relatively high pressure measurements (peak 417). The pressure detected on each finger drops abruptly when the bowler releases the ball (position 411).

Unlike FIG. 3, the amplitude of pressures on the second and third fingers (120 and 130 from FIG. 1 respectively) are not consistent between the first peak 415 and the second peak 417. This is because the action performed by the second and third fingers (120 and 130 from FIG. 1) are different during an actual approach and release of a bowling ball as compared to simply swinging the ball back and forth. During the backswing, gravity and momentum move the ball downward. The second and third fingers (120 and 130) are used to guide the direction of the ball movement and to counteract any forces applied by the thumb. However, when the bowler moves the ball forward, inertial forces exist between the ball and the fingers as it is pushed forward. Because the fingers are used to affect the angle and magnitude of spin (as will be discussed in detail below), the pressures applied to the fingers during the release will be greater than during the backswing.

The data provided in such a comparison graph provides useful information to a bowler or a coach. For example, at the first peak 415, the pressures detected on all three fingers are fairly consistent between Shot 1 and Shot 2. The amplitudes and rate of change are similar. However, at the second peak 417, the maximum pressure exerted by the thumb 150 is greater in the data from Shot 2 than it is in the data from Shot 1. Furthermore, the pressure detected on the third finger 130 at the second peak 417 increases more quickly in Shot 2 than it does in Shot 1. Also, there is a distinct second spike in pressure detected at each finger during the release of Shot 1 (at the second peak 417). As discussed previously, these double spikes could indicate that the bowler has grabbed the ball during her release. These dual pressure spikes affect the movement of the ball during the release and, therefore, affect the performance of the ball after the release.

The performance inconsistencies of the bowler demonstrated in FIG. 4 can be used to determine several different things depending upon the situation in which it arises. For example, a coach has directed his student to throw the same straight bowling shot twice and records the pressure data displayed in FIG. 4. From the data sets of Shot 1, the coach determines that the bowler's release should be modified. The dual pressure spikes from each finger at peak 417 indicate that the bowler grabbed the ball at the last moment. This was possibly an attempt to correct the direction or speed of the ball before releasing.

By adding the data sets of Shot 2 the bowling coach receives a further indication that the bowler's release is inconsistent. As discussed above, the amplitude of the pressure on the thumb 150 is fairly consistent between Shot 1 and Shot 2 during the backswing (peak 415). However, before the release (peak 417), the amplitude of the thumb pressure is noticeably higher during Shot 2 than it is in Shot 1. Based upon this information, the bowling coach further identifies the grip during release as an area that could benefit from coaching.

As the bowler progresses through training, the dual spikes in finger pressure should be more infrequent and the amplitude of pressure during release should become more consistent. This analysis provides the bowler and the coach with a metric by which to quantify improvement.

In another example, an equipment fitter can use this analysis to comparatively identify the best ball and drilling for a particular bowler. The equipment fitter will instruct the bowler to perform two repetitions of the same bowling motion—the first with one type of bowling ball and the second with a different ball. Looking to the plotted data, the equipment fitter can determine, for example, that the second ball is a better fit for the bowler, because she felt compelled to grab the first ball during the release as demonstrated by the dual spikes observed at 432, 434, and 436.

The equipment fitter also instructs the bowler to perform several repetitions of the same bowling motion with the same bowling ball. This time, instead of comparing data sets from one bowling ball to data sets from another, the equipment fitter compares multiple data sets from the same ball. As discussed above, there are inconsistencies detected in the graph of FIG. 4. If those inconsistencies are not present in data sets collected with a different bowling ball, the equipment fitter will conclude that the ball used in FIG. 4 was not appropriate for this bowler.

Without pressure sensing equipment, a bowler might not detect soreness that indicates an improper equipment fit until after bowling several frames. In addition to the comparative analysis discussed above, the equipment fitter can monitor the amplitude of the measured pressures as shown in FIG. 4. If, for example, the equipment fitter determines that pressure over 30 PSI will cause premature soreness in this particular bowler, the equipment fitter can conclude that the ball used in the second throw in FIG. 4 is inappropriate for the bowler because the maximum pressure during the release exceeded the threshold. The threshold may be higher or lower than 30 PSI depending upon the particular bowler and her bowling style.

Although only two data sets are shown for each finger in FIG. 4, more accurate conclusions may be reached by comparing collected pressure data from more than two repetitions of the bowling motion. Depending upon the situation, ten repeated bowling motions may be appropriate.

Figure 5:
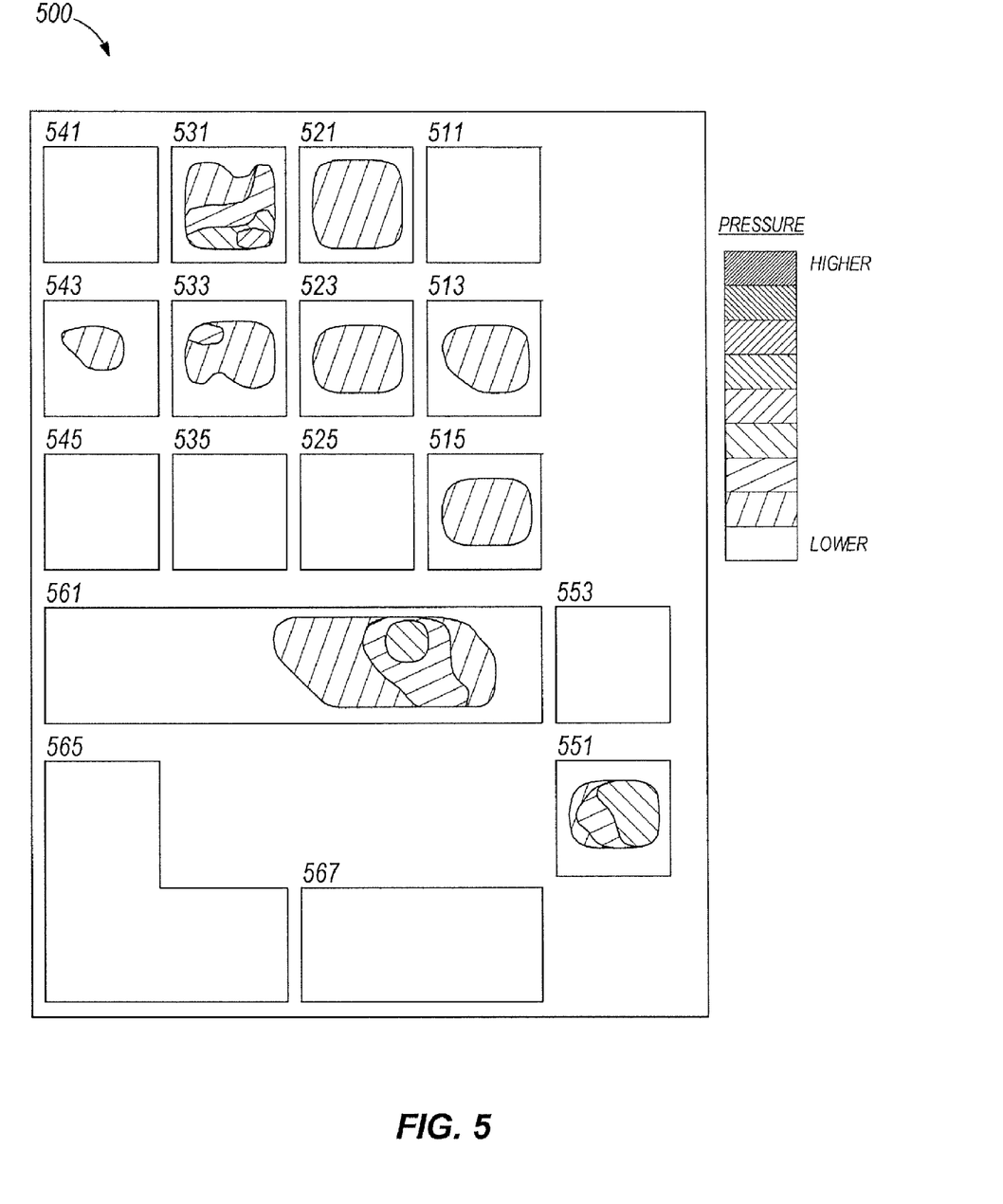
FIG. 5 is an illustration of one construction of a graphical display showing pressures recorded by the system of FIG. 2 during a bowler's normal ball release.
Figure 6:
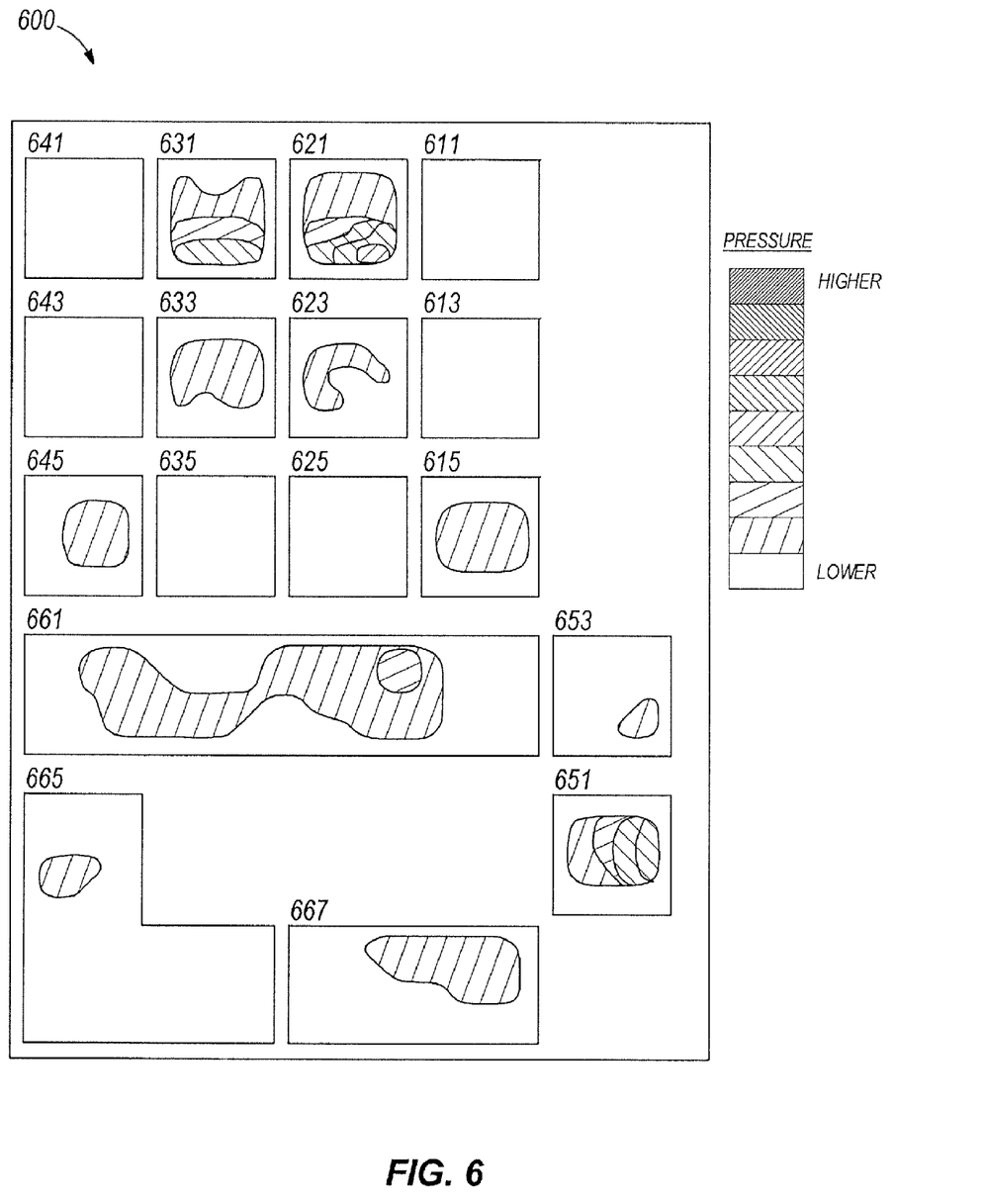
FIG. 6 is an illustration of one construction of a graphical display showing pressures recorded by the system of FIG. 2 during a bowler's ball release resulting in an axis of ball rotation that is more angled than the release of FIG. 5.
Figure 7:
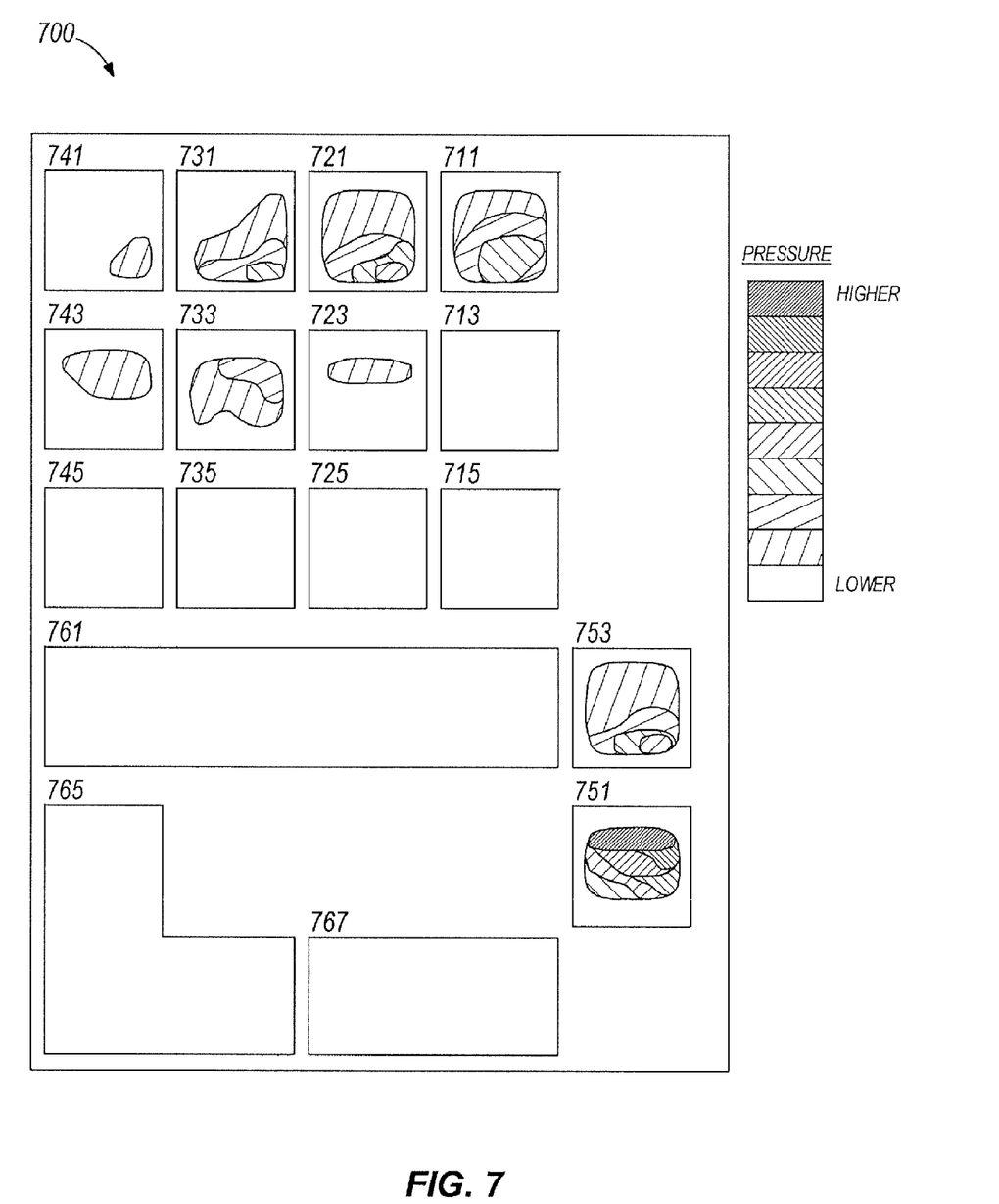
FIG. 7 is an illustration of one construction of a graphical display showing pressures recorded by the system of FIG. 2 during a bowler's ball release resulting in a rate of ball rotation that is higher than the release of FIG. 5.

As discussed above, the pressure sensing apparatus includes multiple pressure sensors that provide pressure information from multiple portions of the bowlers hand and not only the finger tips. This additional information can be beneficial in teaching releases to a bowler. FIGS. 5-7 depict graphical displays that show the pressures detected on each sensor of pressure sensing apparatus 100. Pressure sensors and the corresponding data displays have similar reference characters in the 500, 600, and 700 series for FIGS. 5, 6, and 7, respectively. For example, pressure detected at sensor 131 is displayed at 531 in FIG. 5, at 631 in FIG. 6, and at 731 in FIG. 7.

FIGS. 5-7 show pressure distributions of the ball on the hand as the bowler holds the ball before the approach. FIG. 5 shows the distribution of the ball weight for a bowler before making his primary release. Display section 561 shows the ball resting at the base of the first finger 110 and the base of the second finger 120. For this bowler, the distribution of ball weight shown in FIG. 5 results in a 50 degree axis of rotation and 400 rpms when the ball is released.

FIG. 6 depicts the distribution of ball weight for the same bowler, this time applying a greater angle of axis rotation. Display sections 661, 665, and 645 show that the distribution of weight before the approach is shifted toward the base of the fourth finger 140 and toward the edges of the palm of the bowler's hand. This distribution of weight resulted in a 75 degree axis of rotation.

FIG. 7 depicts the distribution of ball weight for the same bowler when applying a higher rate of rotation. As indicated by display section 761, the weight of the ball has been moved off of the base of the bowler's fingers and, as indicated by display sections 751 and 753, the weight has been shifted to the base of the bowler's thumb. Additionally, the first finger 110 provides more pressure as indicated by display section 711.

As FIGS. 5-7 and the discussion above demonstrates, the speed and angle of rotation of the bowler's ball after the release can be influenced by shifting the position of the ball before the approach and maintaining this distribution through the release. If the bowler wishes to add more spin to the ball, the coach can instruct the bowler to shift the weight of the ball toward the fourth finger 140. Conversely, if the bowler complains of too much spin causing the ball to move toward the gutter of the alley after release, the coach can instruct the bowler to shift the weight of the ball toward the thumb 150. Progress can be monitored by displaying data in a format similar to that depicted in FIGS. 5-7. Additionally, the coaching and equipment fitting methods discussed above in reference to FIG. 4 may also be applied to pressures as monitored and analyzed through the displays of FIGS. 5-7.

It should be understood that the constructions and methods described above are exemplary and other configurations and designs are possible. For example, additional components, sensor arrangements, or automated operations may be added to the described constructions and methods without departing from the intended scope. Various features and advantages of the invention are set forth in the following claims.

What is claimed is:

1. A bowling grip pressure device comprising:
    a glove including
        a first finger sheath positioned to accept and cover a first finger,
        a second finger opening positioned to accept and leave substantially exposed a second finger,
        a third finger opening positioned to accept and leave substantially exposed
        a third finger,
        a fourth finger sheath positioned to accept and cover a fourth finger, and
        a thumb opening positioned to accept and leave substantially exposed a thumb; and
    a plurality of pressure sensors including
        a first pressure sensor configured to be temporarily attached to the substantially exposed second finger,
        a second pressure sensor configured to be temporarily attached to the substantially exposed third finger,
        a third pressure sensor configured to be temporarily attached to the substantially exposed thumb, and
        at least one pressure sensor permanently affixed to the glove.

2. The bowling grip pressure device according to claim 1, wherein
    the first pressure sensor is configured to be temporarily attached to the substantially exposed second finger between a second finger tip and a second distal interphalangeal joint when worn,
    the second pressure sensor is configured to be temporarily attached to the substantially exposed third finger between a third finger tip and a third distal interphalangeal joint when worn, and
    the third pressure sensor is configured to be temporarily attached to the substantially exposed thumb between a thumb tip and a thumb proximal interphalangeal joint when worn.

3. The bowling grip pressure device according to claim 1, wherein the at least one pressure sensor permanently affixed to the glove includes:
    a fourth pressure sensor affixed to the first finger sheath and positioned so as to align between a first finger tip and a first distal interphalangeal joint when worn, and
    a fifth pressure sensor affixed to the fourth finger sheath and positioned so as to align between a fourth finger tip and a fourth distal interphalangeal joint when worn.

4. The bowling grip pressure device according to claim 1, wherein the at least one pressure sensor permanently affixed to the glove includes:
    a pressure sensor positioned so as to align with the metacarpophalangeal joint of at least one of the first finger, the second finger, the third finger, and the fourth finger when worn.

5. The bowling grip pressure device according to claim 1, wherein the at least one pressure sensor permanently affixed to the glove is positioned so as to align with a bowler's palm when worn.

6. The bowling grip pressure device according to claim 1, further comprising:
    a processor configured to record pressure data from each of the plurality of pressure sensors as a function of time; and
    a communication interface connecting the plurality of pressure sensors to the processor.

7. The bowling grip pressure device according to claim 6, wherein the communication interface includes a wireless communication device.

8. The bowling grip pressure device according to claim 7, wherein the wireless communication device includes a radio frequency transmitter coupled to the plurality of pressure sensors and a radio frequency receiver coupled to the processor.

9. The bowling grip pressure device according to claim 6, wherein the interface includes a serial communication cable.

10. The bowling grip pressure device according to claim 1, wherein the plurality of pressure sensors further includes:
    pressure sensor affixed to the first finger sheath and positioned so as to align between the first distal interphalangeal joint and a first proximal interphalangeal joint when worn,
    a pressure sensor configured to be temporarily attached to the substantially exposed second finger between the second distal interphalangeal joint and a second proximal interphalangeal joint when worn,
    a pressure sensor configured to be temporarily attached to the substantially exposed third finger between the third distal interphalangeal joint and a third proximal interphalangeal joint when worn, and
    pressure sensor affixed to the fourth finger sheath and positioned so as to align between the fourth distal interphalangeal joint and a fourth proximal interphalangeal joint when worn.

11. The bowling grip pressure device according to claim 1, wherein the plurality of pressure sensors further includes:
    a pressure sensor affixed to the first finger sheath and positioned so as to align between the first proximal interphalangeal joint and a first metacarpophalangeal joint when worn,
    a pressure sensor configured to be temporarily attached to the substantially exposed second finger between the second proximal interphalangeal joint and a second metacarpophalangeal joint when worn,
    a pressure sensor configured to be temporarily attached to the substantially exposed third finger between the third proximal interphalangeal joint and a third metacarpophalangeal joint when worn,
    a pressure sensor affixed to the fourth finger sheath and positioned so as to align between the fourth proximal interphalangeal joint and a fourth metacarpophalangeal joint when worn, and
    a pressure sensor configured to be temporarily attached to the substantially exposed thumb between the thumb proximal interphalangeal joint and a thumb metacarpophalangeal joint when worn.

12. A method of analyzing a bowler's performance, the method comprising:
    performing a plurality of bowling motions;
    measuring a pressure exerted on each of a second finger, a third finger, and a thumb during each of the plurality of bowling motions;

recording the measured pressures as a function of time to create a measurement set for each of the plurality of bowling motions; and evaluating the bowler's performance based upon the recorded pressures as a function of time.

13. The method according to claim 12, wherein performing a plurality of bowling motions includes performing ten throws of a bowling ball.

14. The method according to claim 12, further comprising measuring the pressure exerted on a first finger and a fourth finger during each of the plurality of bowling motions.

15. The method according to claim 12, further comprising correlating the measured pressures as a function of time to physical positions of the bowler during the bowling motion.

16. The method according to claim 15, wherein correlating the measured pressures includes:

identifying a first period of relatively high pressure measurements as a position near the end of a bowler's backswing; and identifying a second period of relatively high pressure measurements as a position prior to releasing the bowling ball.

17. The method according to claim 12, wherein evaluating the bowler's performance includes:

detecting a first period of relatively high pressure measurements and a second period of relatively high pressure measurements in the measurement set for each of the plurality of bowling motions;

calculating an elapsed time between the first period of relatively high pressure measurements and the second period of relatively high pressure measurements for each of the plurality of bowling motions;

comparing the calculated elapsed times for each of the plurality of bowling motions; and identifying a variation in elapsed time for at least one of the plurality of bowling motions.

18. The method according to claim 12, wherein evaluating the bowler's performance includes:

detecting a first period of relatively high pressure measurements in the measurement set for each of the plurality of bowling motions;

determining a maximum measured pressure in the first period of relatively high pressure measurements in the measurement set for each of the plurality of bowling motions for at least one of the second finger, the third finger, and the thumb;

comparing the maximum measured pressure in the first period of relatively high pressure measurements for each of the plurality of bowling motions; and identifying a variation in maximum measured pressure for at least one of the plurality of bowling motions.

19. The method according to claim 12, wherein evaluating the bowler's performance includes:

detecting a second period of relatively high pressure measurements in the measurement set for each of the plurality of bowling motions;

determining a maximum measured pressure in the second period of relatively high pressure measurements in the measurement set for each of the plurality of bowling motions for at least one of the second finger, the third finger, and the thumb;

comparing the maximum measured pressure in the second period of relatively high pressure measurements in the measurement set for each for the plurality of bowling motions; and identifying a variation in the maximum measured pressure in the measurement set for at least one of the plurality of bowling motions.

20. The method according to claim 12, wherein evaluating the bowler's performance includes:

identifying an increase or decrease in pressure amplitude that is not consistent with a curvilinear shape in the measurement set for at least one of the plurality of bowling motions.

21. A method of fitting a bowler with a bowling ball, the method comprising:

performing a first bowling motion with a first bowling ball;

measuring pressure exerted on each of a second finger, a third finger, and a thumb during the first bowling motion;

recording the measured pressures as a function of time to create a first set of measurements; and evaluating a fit of the first bowling ball for the bowler based upon the recorded pressures as a function of time.

22. The method according to claim 21, further comprising:

performing a second bowling motion with a second bowling ball;

measuring a pressure exerted on each of the second finger, the third finger, and the thumb during the second bowling motion; and recording the measured pressures as a function of time to create a second set of measurements, wherein evaluating a fit of the first bowling ball includes comparing the first set of measurements as a function of time to the second set of measurements as a function of time.

23. The method according to claim 22, wherein the second bowling ball is a different type of bowling ball with the same drilling as the first bowling ball.

24. The method according to claim 22, wherein the second bowling ball is the same type of bowling ball with a different drilling than the first bowling ball.

25. The method according to claim 21, further comprising:

repeating the bowling motion a first plurality of times with the first bowling ball;

measuring pressure exerted on each of the second finger, the third finger, and the thumb during each of the first plurality of times; and recording the measured pressures as a function of time to create a first plurality of measurement sets, and wherein evaluating a fit includes determining a consistency of bowler performance with the first ball by detecting deviations in pressure as a function of time between the first set of measurements and the first plurality of measurement sets.

26. The method according to claim 25, further comprising repeating the bowling motion a second plurality of times with a second bowling ball;

measuring pressure exerted on each of the second finger, the third finger, and the thumb during each of the second plurality of times; and recording the measured pressures as a function of time to create a second plurality of measurement sets, and wherein evaluating a fit further includes determining a consistency of bowler performance with the second ball by detecting deviations in pressure as a function of time between the second plurality of measurement sets, and comparing the consistency of bowler performance with the first ball to the consistency of bowler performance with the second ball.

27. The method according to claim 21, wherein evaluating a fit includes detecting an increase or decrease in pressure amplitude as a function of time in the first set of measurements that is not consistent with a curvilinear shape.

28. The method according to claim 21, wherein evaluating a fit includes:
   determining a maximum measured pressure for at least one of the first finger, the second finger, and the thumb; and
   comparing the maximum measured pressure to a threshold value.

* * * * *